United States Patent
Kieval et al.

(10) Patent No.: US 6,190,324 B1
(45) Date of Patent: Feb. 20, 2001

(54) IMPLANTABLE MEDICAL DEVICE FOR TRACKING PATIENT CARDIAC STATUS

(75) Inventors: Robert S. Kieval, Golden Valley; Kenneth M. Riff, Plymouth, both of MN (US)

(73) Assignee: Medtronic, Inc., Minneapolis, MN (US)

( * ) Notice: Under 35 U.S.C. 154(b), the term of this patent shall be extended for 0 days.

(21) Appl. No.: 09/301,206

(22) Filed: Apr. 28, 1999

(51) Int. Cl.$^7$ .................................................... A61B 5/04
(52) U.S. Cl. ........................................... 600/483; 600/510
(58) Field of Search .............................. 600/483, 510, 600/513; 607/18, 19, 20, 27

(56) References Cited

U.S. PATENT DOCUMENTS

| | | | |
|---|---|---|---|
| 4,716,903 | 1/1988 | Hansen et al. | 128/419 PG |
| 4,791,935 | 12/1988 | Baudino et al. | 128/634 |
| 4,903,701 | 2/1990 | Moore et al. | 128/419 PG |
| 4,938,228 | 7/1990 | Righter et al. | 128/690 |
| 5,039,492 | 8/1991 | Saaski et al. | 422/82.09 |
| 5,086,772 | 2/1992 | Larnard et al. | 128/419 D |
| 5,113,869 | 5/1992 | Nappholz et al. | 128/696 |
| 5,199,428 | 4/1993 | Obel et al. | 128/419 C |
| 5,292,340 | 3/1994 | Crosby et al. | 607/17 |
| 5,300,093 | 4/1994 | Koestner et al. | 607/32 |
| 5,309,919 | 5/1994 | Snell et al. | 128/697 |
| 5,312,446 | 5/1994 | Holschbach et al. | 607/9 |
| 5,313,953 | 5/1994 | Yomtov et al. | 128/696 |
| 5,365,934 | 11/1994 | Leon et al. | 128/707 |
| 5,404,877 | 4/1995 | Nolan et al. | 128/671 |
| 5,411,031 | 5/1995 | Yomtov | 128/706 |
| 5,518,001 | 5/1996 | Snell | 128/697 |
| 5,533,957 | 7/1996 | Aldea | 600/16 |
| 5,749,900 | 5/1998 | Schroeppel et al. | 607/4 |
| 5,882,936 | 3/1999 | Benstsen et al. | 436/68 |

FOREIGN PATENT DOCUMENTS

| | | | |
|---|---|---|---|
| 9834537 | 8/1998 | (WO) | A61B/5/0205 |

Primary Examiner—William E. Kamm
(74) Attorney, Agent, or Firm—Michael B. Atlass; Harold R. Patton

(57) ABSTRACT

An implantable medical device determines activity levels and Heart Rate and from a combination of these produces a value for a heart rate activity coefficient (HRAC). This value has significant diagnostic and patient tracking value. Methods and apparatus for determining this HRAC value are described. This enables physician review of patient cardiac status. Additional physiologic data can be recorded along with the HRAC data if desired, and this too, as well as the HRAC data alone, may be reported out from the implanted device to a medical communications system for alarm purposes, titrating drugs/therapies or other monitoring tasks. Further, substitutes for heart rate measurements and activity measurements are described which can be used to augment or substitute for heart rate measurements and activity measurements. These substitutes should represent cardiovascular or cardiac responsiveness to substitute for heart rate in the HRAC signal; and should represent cardiac demand to substitute for activity in the HRAC signal.

28 Claims, 5 Drawing Sheets

IMPLANTABLE MEDICAL DEVICE FOR TRACKING PATIENT CARDIAC STATUS

This invention relates to the field of implantable medical devices for enabling enhanced medical monitoring of patients, most particularly for use with heart rate together with activity sensing, and has application to the field of monitoring patients generally and particularly those with conditions such as Congestive Heart Failure (CHF).

BACKGROUND

There are numerous devices both implantable and external that have been used to monitor various patient medical conditions. Well known for heart patients is the Holter monitor which permits somewhat uncomfortable monitoring of an electrocardiogram for 24 hours which can then be read by a physician to find anomalies in the rhythm which were not susceptible to discovery or confirmation in a patient's visit to the doctor's office. A number of other devices have improved on the ability to maintain records of electrocardiograms and numerous other health related patient parameters and even device performance parameters. Implantable medical devices such as pacemakers and Implantable Cardioverter/Defribrillators (ICDs) and even non-therapeutic monitoring devices are currently capable of maintaining some records and reporting out such data. An example of a non-therapy delivering monitoring implantable medical device can be seen in U.S. Pat. Nos. 5,313,953 and 5,411,031 issued to Yomtov et al., and in Holsbach et al, U.S. Pat. No. 5,312,446, and others. Nolan et al,'s U.S. Pat. No. 5,404,877 teaches that such devices can even generate patient alarms. All these patents are incorporated herein by this reference in that they provide information about what can currently be done in the implantable device field.

Current generation pacemakers and ICDs have the ability to store different types of information in order to provide feedback to the clinician about the patient/device system. Examples of stored information include arrhythmia diagnostics, histograms of paced and sensed events, electrograms and trends of lead impedance. Such information is useful not only in optimizing device programming but also in the management of the patient's arrhythmias and other conditions. While our invention focuses on the monitoring of patient activity tied to heart rate, which we use as a functional status monitor, the additional information available from implantable devices could be used as an adjunct.

However, to date the literature is devoid of a satisfactory description of how to use activity information. There has been considerable thinking in this area, but none have yet succeeded in producing a satisfactory measure to track patient functional status. Some examples of this thinking in the current literature are described in detail in a application assigned to the assignee of this patent application, with Ser. No. 09/078,221, now U.S. Pat. No. 6,045,513, incorporated herein by this reference in its entirety. This incorporated reference, Ser. No. 09/078,221, now U.S. Pat. No. 6,045,513, also describes in great detail how a simple measure of activity alone can be related to the New York Heart Association classification of CHF patients to provide a status monitor.

As is known in the art, implantable medical devices exist that have various accelerometers and piezo crystal activity sensors and the like which count the movement of the crystal or sensor with respect to a resting state. Medtronic brand implantable medical devices with piezoelectric crystal or accelerometer based activity sensors have the ability to convert a raw activity signal into 2 second activity counts. In other words, the number of times the accelerometer or sensor moves in a two second period is called a 2 second activity count. The prior incorporated '221 application, now U.S. Pat. No. 6,045,513, teaches how to take advantage of such and similar types of data to effectively solve the problems in diagnosis and patient monitoring and tracking a patient's status. It is a well established practice to supply signals from piezocrystals or accelerometers as a measure of metabolic demand.

However, another needed measurement should be available through a device that tracks the patients' natural cardiac responsiveness to stress in a clinically meaningful measurement.

In humans, cardiac output is a function of stroke volume, a reflection of the pumping ability of the heart, and heart rate (sometimes referred to as HR). As people age, or in the presence of conditions that limit the heart's pumping ability, there is a progressive dependence on an increase in HR under conditions such as exercise, during which an increased cardiac output is required. Alternatively, chronotropic incompetence (which we define as an inadequate rise in HR during exercise) may also develop during aging, the progression of heart failure (CHF), or secondary to the use of drugs in the treatment of CHF, hypertension or other diseases. (Such drugs might include beta-blockers, calcium channel blockers, and so forth). This chronotropic incompetence may thus reflect a worsening cardiac status or drug side effects.

Cardiac output is a measurement often useful in characterizing CHF status too. It is measurable by various formulae including the following:

$$CO=(SV)(HR),$$

where Cardiac Output(CO) is measured in volume (liters) per unit time (minutes), Stroke Volume (SV) is measured in liters per beat and Heart Rate (HR) is measured in beats per minute.

Chronic trend data on HR response to exercise could provide information about the degree of dependence on HR to increase the cardiac output, an indicator of the heart's pumping ability. Over time, an increasing HR response to a given level of exercise may indicate worsening cardiac function. Such exaggerated HR response is a prominent finding in the transition from asymptomatic left ventricular dysfunction to symptomatic heart failure. In other words, if there is a trend toward increasing HR response when a similar level of exercise would not have developed the same high HR rate response, the doctor should be concerned about the onset of symptomatic heart failure and decreasing cardiac output capacity. This trend information may also be clinically useful in tracking the degree of chronotropic incompetence.

While chronic 24-hour mean HR may be also monitored, the change in the mean HR could be reflecting changes in the activity levels of the patient and would therefore not be very useful. Chronic resting HR trends can also provide information about an individual's level of cardiovascular functioning or conditioning, but these data also lack specificity for the problems outlined. As was shown in the Ser. No. 09/078,221 application, now U.S. Pat. No. 6,045,513, monitoring the activity alone may be quite useful clinically. However, changes in patient activity levels may also lack specificity and could be related to orthopedic or other problems or factors.

Currently implantable medical devices have the ability to track HR using intracardiac electrocardiograms or subcutaneous electrocardiograms. Likewise chronic trend information can be collected using a standard piezoelectric crystal or with an implanted accelerometer. While each of these provide some insight, the HR measured and related to the activity level may provide the most specific and clinically useful information about the changing cardiac function. However, currently such a measurement is not provided as a separate measurement.

However, there are no devices that can be implanted and provide long term data with a single variable relating cardiac responsiveness to stress. It would therefore be a valuable adjunct to cardiac medicine to have such a device.

Currently, as patients get sicker from CHF, they typically are less and less active. To test them for CHF, physicians may have them do a standardized exercise routine and look for changes in heart rate response to activity over a series of office visits. Having a device capable of making this evaluation without clinic visits and forcing the patient into a stress test would provide a valuable new tool for cardiac physicians.

It is believed that the CHF patient who is deteriorating and having reduced levels of activity will nevertheless show an increase in a factor we identify as a Heart Rate Activity Coefficient (HRAC), but, if the decrease in activity is due to some other cause the HRAC is unlikely to be affected.

Heart rate variability by itself, as is seen in Schroeppel's U.S. Pat. No. 5,749,900, (incorporated herein by this reference) does not provide the same data on the strength of HR responsiveness to activity or HRAC.

SUMMARY OF THE INVENTION

Figure 1:
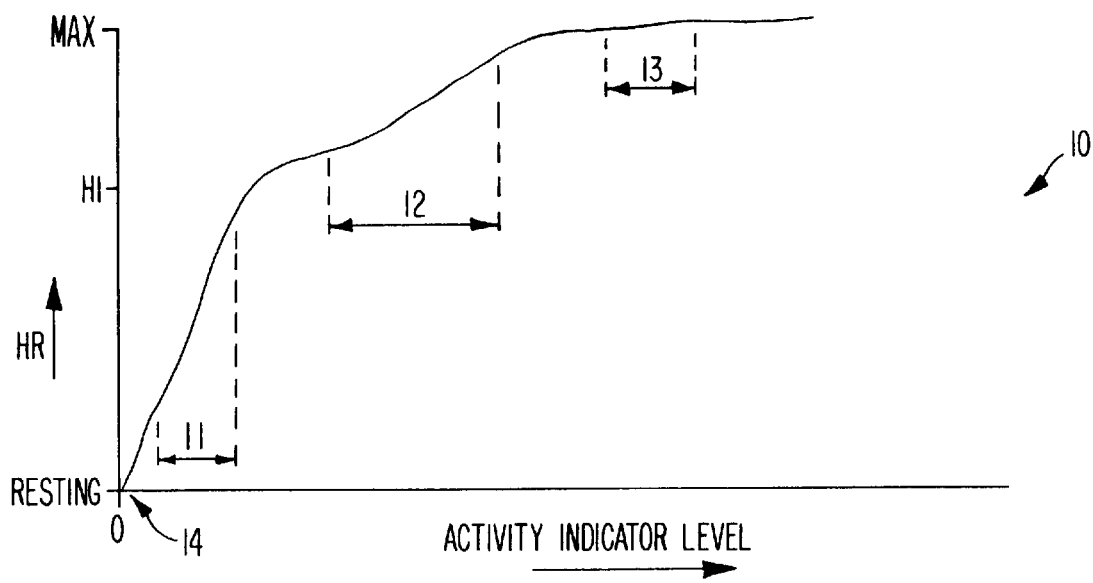
FIGS. 1 and 2 are graphs of Heart Rate versus Activity.

This invention defines a new clinical variable, which may be termed the Heart Rate Activity Coefficient (HRAC), and describes its use in monitoring cardiac function in an implanted device capable of monitoring heart rate and some measure of activity like acceleration. This coefficient may be considered a variable which can be stored and reported by any implantable device, including but not limited to, standard cardiac pacemakers, implantable cardioverter/defibrillators (ICDs) or even by simple implantable medical devices which only monitor this variable, or ones which monitor this variable and other physiologic parameters.

Generally, the heart rate for a short period is stored together with the acceleration or activity data signal for the same period. The HRAC value may be calculated across a serially collected set of such periods as a slope. Other measures and variants of this particular HRAC value may be determined and used and these are described as well. A relatively large variety of implantable medical devices can be employed to implement the determination of HRAC values and may be used to deploy HRAC histograms and analyze HRAC values for downstream activities such as research, drug titration, patient care, alarm setting and the like. Over time, the HRAC measurement, however it may be determined, provides an individualized progression chart of the patent's cardiac function. The alarm could be set based on the HRAC reaching a preset or physician programmed level or matching a pattern of slope or rise time that has been similarly preset or programmed. Also the alarm can be based on a patient trigger and programmed as desired.

Likewise, deciding when to capture the HRAC value may be triggered based on either HR or activity levels. Further, we also identify that other physiologic signals which may come from independent sensors could be used to substitute for heart rate in the HR part of the HRAC value or in activity in the activity portion of the HRAC value we are measuring and these too could be used to trigger the measurement and subsequent storage of the HRAC values. Respiratory rate would be one such substitute signal. Cyclic variation in the rate of pressure change on a lead in a heart chamber could be another example. Others are mentioned in some detail within. The preferred cardiac response parameter is heart rate. The flexibility to choose alternatives to accelerometer count based activity levels is much broader. Further, use of mixed activity type signals in generating an HRAC signal is also described.

DETAILED DESCRIPTION OF PREFERRED EMBODIMENTS

Nearly any currently implanted medical devices could be adapted to employ the features of this invention provided only that such a device maintains either a direct and constant link with a memory device or has its own memory device and its own activity sensor, and that there is provided an appropriate processing circuit or program to enable the invention activity. Activity sensors are well known and have been employed in pacemaker type implantable medical devices for many years. A typical such device is seen in Strandberg's U.S. Pat. No. 4,886,064, and it is now common to see the basic activity sensor combined with alternative means for sensing activity such as minute ventilation as in U.S. Pat. No. 5,562,711, both of which are hereby incorporated by this reference in their entireties.

Sensors for measuring pressure, temperature, posture, impedance and the like, as well as various combinations of such sensor signal output, have been used for making judgments about appropriate heart rates for cardiac pacemakers based on an assumed correspondence of their output and activity or cardiac demand. It is contemplated within the scope of this invention that such sensor output can be easily employed in the same capacity as the activity values we describe being generated from activity sensors or accelerometers in our most preferred embodiments, without undue experimentation. So long as there is a correspondence in time between the collection of the activity-type signal and the measured or determined HR, the operative principals of this invention apply.

Heart rate monitoring is known and has been used in simple wrist worn devices such as the one described in U.S. Pat. No. 4,938,228 to Righter et al (incorporated herein by this reference) as well as into exercise equipment (see for example, U.S. Pat. No. 5,365,934 to Leon, et al, also incorporated herein by this reference). However, the art does not appear to correlate these signals of heart rate to cardiac response to provide a convenient measure of cardiac function or chronotropic competence as we have.

Figure 6:
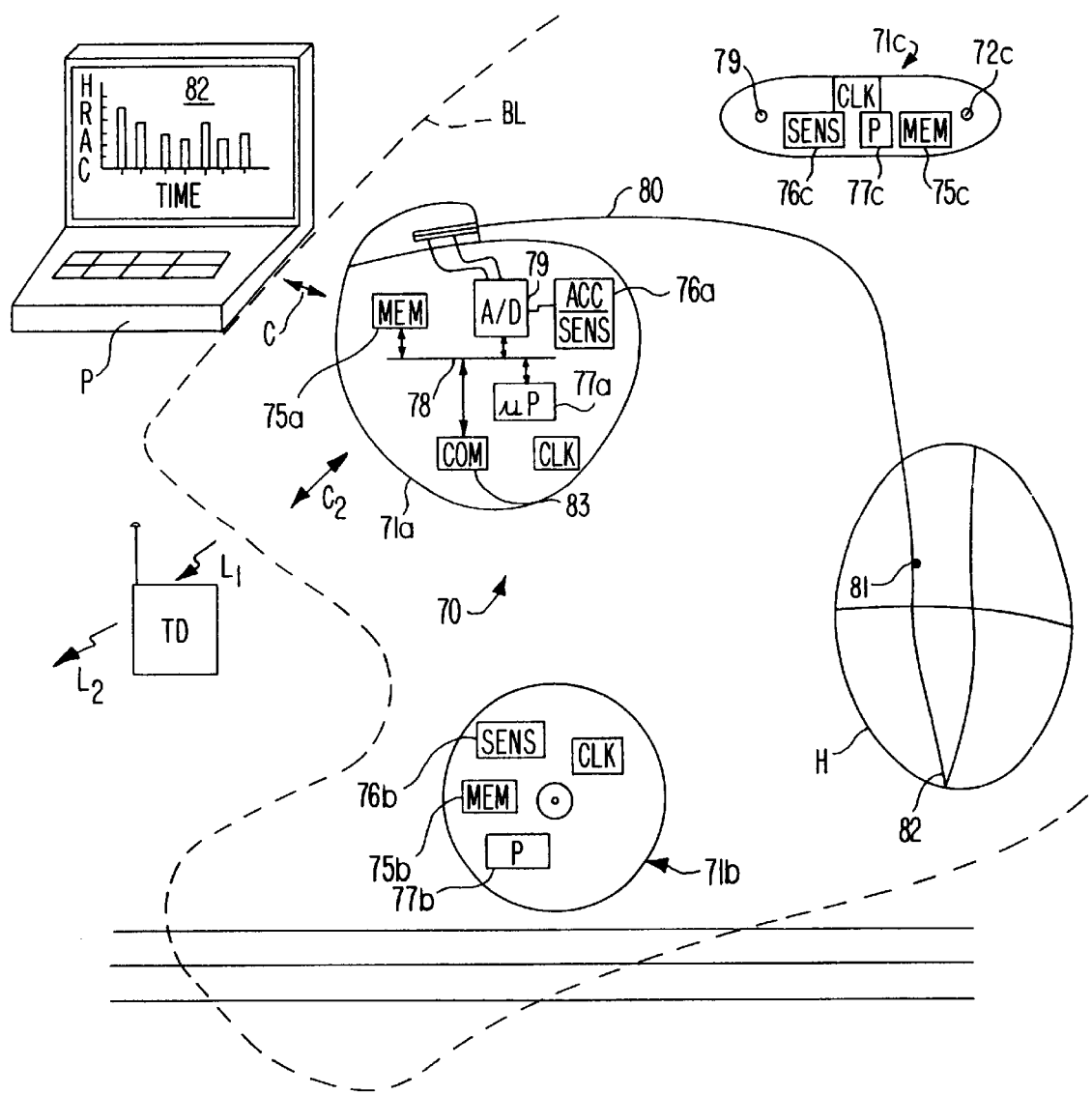
FIG. 6 is a drawing of the inside of a patient's body having three implants within it on the right side of a line BL and an external programmer for communication with the implantable devices.

To describe the preferred context for using such a measure we refer now to FIG. 6, in which a set of alternative implantable devices 71a–c are illustrated inside of a patient body, (the edge of which is here illustrated as line BL,) the typical application of this invention will be to provide data for a display 82 on an external device such as a programmer P external to the patient body, via a communications channel such as is here represented by double headed arrow C. The data may be shown in the form of a bar chart or line graph or similar display which indicates the total amount of some algorithmically derived measure of the Heart Rate Activity Coefficient (HRAC) over a given period of time, such as months, weeks, days or hours. Device 71a is a pacemaker having a memory 75a which stores the data measured by the sensor 76a. The storage can be in a raw form if there is sufficient memory or it can be compressed in various advantageous forms by a program or other circuit device running a process such as processor 77a. In a preferred embodiment, the microprocessor 77a runs a program stored in memory to convert sensed activity counts processed through an analog to digital converter 79 as they appear on a bus 78, and then returns the processed data to the program for temporary storage in the memory circuit 75a. When enough measurements are made in accord with the program, the microprocessor converts a representation of the total to a value and stores the representation in the memory.

There are other ways to store activity related data, of course, such as average counts over a given time period, peak excursions over a time period, the average range over a time period, and so forth. Any method based on sensors or sensing that gives an indication of activity occurring in a short period of time may be useful for deriving the HRAC measurement. As just above mentioned, one may use other indications besides motion, but not limited to including breathing rate or minute ventilation, body orientation, pressure, temperature, or some combination of any of these, if desired.

Of course, we also have to determine heart rate. Many methods have been found to do this, including through acoustic sensors, an accelerometer on an indwelling lead in a ventricle, impedance measurements of the blood volume in the heart or a chamber thereof, electrocardiographic analysis based on peak to peak amplitude measurements and the like, all generally well known and based on a periodically oscillating signal value, the periodicity of which indicates the rate. For example, when an R-wave passes as indicated by a cardiac electrogram measurement of the passing of a peak amplitude signal, until the next R wave of similar amplitude height, a time measurement is made. This is the R—R interval value. An interval value is the inverse of heart rate. (Thus an R—R interval of 1000 milliseconds is 60 beats per minute). There are many variations on how to determine HR and they are well known, and any of these of reasonable accuracy can be used for the purposes of the invention herein. For a simple particular method, a count of time units or clock cycles per R-wave signal in an input electrocardiogram signal stream may be monitored and a value computed based on this measure and stored in memory by a processor. The R-waves themselves may be found in variation in electrocardiogram amplitude signals by finding the peaks or level crossing detection or in many other ways currently known. At the time of the storing of an HR value for the HR variable for a given time period comprised of a number of clock cycles/time units, a value is stored for the level of patient activity. These two values (HR and "activity" or cardiac demand) can be combined in a combination routine or through an analog process if desired or they may be stored independently, preferably in a memory as digital values, for later retrieval and manipulation by a program in an external device if desired. In any event, the combination of HR and activity value for each time must be stored somewhere to display a plot of HRAC over time, or to provide any other useful application of this set of data values.

If the trajectory of the value of HRAC or the particular value of HRAC at a given time is above a level determined to be dangerous, the device can contact the medical service handling the patient who has the implanted device. A regular report could be sent through a device like device TD (FIG. 6) or to a programmer P during clinical visits whereupon the physician can review the patient's status and the HRAC histogram derived from the HRAC data values stored over time in the patient's implantable medical device.

It is important to recognize that while we prefer to employ heart rate vs. activity (as measured by accelerometer counts for example) for determining an HRAC value, there are reasonable alternatives. Heart Rate however is purely a cardiac response measure and easily found. Activity is also easily found and purely a metabolic demand parameter (assuming it is filtered for motion artifacts and the like). When employing such alternatives parameters, for example respiratory rate, there are factors of both cardiac responsiveness and of cardiac demand inherent in such a signal.

Parameters which could bolster or substitute for heart rate or activity in the HRAC measurement as described include respiratory rate, oxygen saturation in the coronary sinus and elsewhere, pH in the coronary sinus, stroke volume (an especially good alternative for heart rate), QT interval, level of blood pressure regulating hormones and so forth. Again, one of these could substitute for activity in determining cardiac demand, or metabolic demand.

Therefore, a first benefit to using both an accelerometer signal and a respiratory rate, blood oxygen saturation level, and the like is to exclude false signals from one or the other. For example, the respiratory rate will not rise from driving down a bumpy road but the accelerometer count will.

A second benefit can come from using a combined value. In the use of accelerometers and piezo crystal activity sensors with respiratory rate related sensors to determine pacing rate, a correspondence between metabolic demands and the curves of such signals are worked out so as to provide the most likely proper rate responsive to the actual metabolic demand. Employment of such systems to determine a trigger point for measuring HRAC value would be useful.

A third benefit would come from the use of these independently to produce paired HRAC values and thus two HRAC trends. The review of these trends together will yield clinically useful information.

Storage of these values can be done in various ways too. Thus a variable for a given time period could represent the peak activity during a time period, the average for the time period, the peak sustained for more than a given subset of a time period, the range over a time period, and so forth. This variable may then be added to, subtracted from, divided by or otherwise combined with the heart rate taken for the same period, and the result of this combination will be the value of the HRAC variable for the period.

Since the same combination (by addition, subtraction, etc.) of values will be done for each period, the running variation, trend or slope in the HRAC value will in whatever the chosen combination, represent the slope of the HRAC which is what is of concern. Thus if a patient on a particular day has a HR of 60 bpm at an activity level of 3 and a HR of 80 at an activity level of 4 during one period, and in a second period (perhaps a week or several months later) is exhibiting a HR of 60 at 3 and a HR of 100 at an activity level of 4, it would be quite easy to see the change in cardiac responsiveness. Using this convenient set of numbers it is easy to find a formula to generate HRAC numbers that show this change. A simplest set would be: (HR2−HR1)/(AL2−AL1) for the first time period HRAC value, then (HR4−HR3)/(AL4−AL3) for the second HRAC value. For the present set of numbers that would be (80−60)/(4−3) or (20)/(1); or 20 for the first HRAC value and (100−60)/(4−3), or (40)/(1) or 40 for the second HRAC value, thus showing a positive trend. The preferred formula for any particular embodiment will depend upon the memory capacity and structure, the processing power and the resolution desirable for the particular implementation. Thus (HR1+HR2+HR3 . . . +HRN)/(AL3) may be appropriate in some situations and for those in which a broader numerical spread in the overall movement of HRAC value might be of interest use ((HR1+HR2+HR3 . . . +HRN)/N)(AL3). Likewise a single HR value could be weighted for a given activity slope picked out in a line of activity values measured over time as in a formula wherein; if the activity is over 3 but less than 6 for a period of five minutes pick the HR value of the start of minute 5, as the HRAC value, for example. Also a trigger to save an average HR value over the 4th or 5th minute would be good too, for this last example as the HRAC value. As mentioned elsewhere, the HR itself could act as a trigger. Thus if HR=85 for over 30 seconds, a program could be initiated to check the activity value and store one of the possible measures of HRAC if the activity level is below 10 or above 6. As can be seen there is a large realm of potential HRAC measures that would be useful to capture. The important value is repeatability so that whatever value is captured, the same value is captured for a similar activity profile or level over time.

Additional calculations can also derive other metrics of interest, such as slope of the slope (second derivative) of the HRAC values.

Review FIG. 1, wherein heart rate (HR) is plotted against the activity indicator level in the curve on graph 10. At the resting level 14 there is a resting level of activity (essentially zero) and a resting heart rate (commonly 50–70 bpm). Typically, in the first phase of exercise, a strong upward slope of increase in HR occurs as the activity level increases, resulting in an often quite consistent period of steady upward slope on this curve, here at segment 11. As exercise continues to increase giving an activity level signal additional areas of steady increase like area 12 will be seen, after the initial ramp up from resting state. Finally, there will be a maximum HR at a certain level of exercise with a zero (or close to it) slope at segment 13. Several similar measures or others like them can be used. For examples, the rate of change in HR during these consistent slope periods, a measure of HR taken at a mid section, or other point within one of these segments 11, 12, or 13, or an average HR for the period of the steady slope segment can be used as the measure of HR of merit for this invention to be reported as HR at an activity level for the segment. This will be the HRAC measure.

Figure 2:
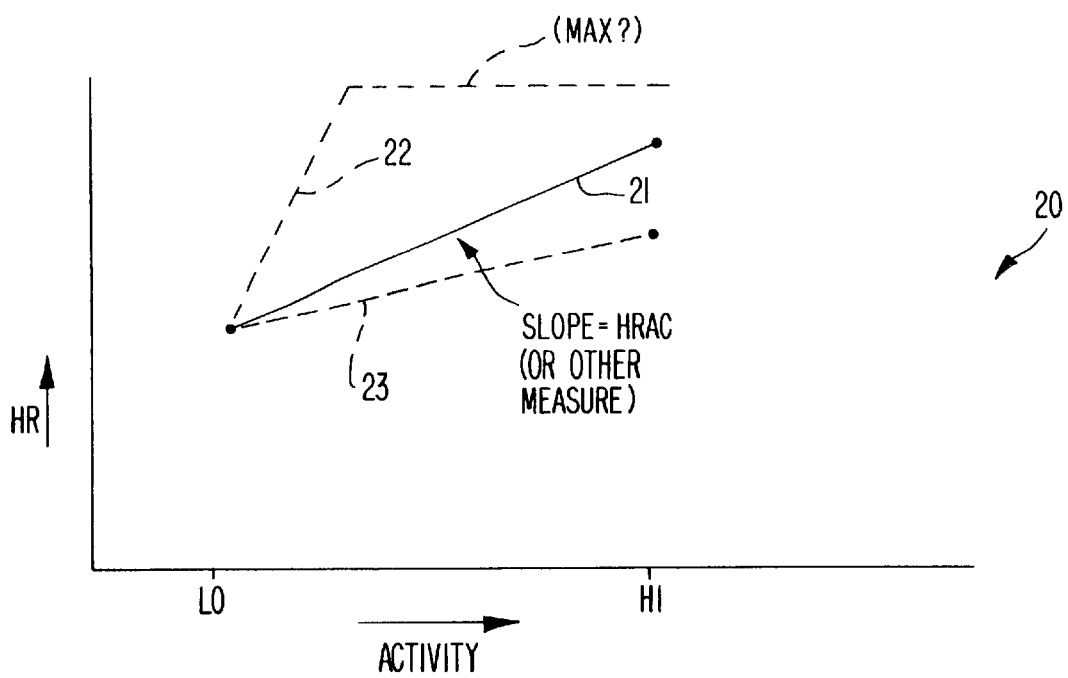

Referring to FIG. 2, the graph 20 of this the simplified view indicates that HRAC may be the simple slope of HR and activity level plotted as a line. Here the line 21 may represent normal HR response to activity, the steeper sloped line 22, indicates a worsening condition and the lower sloped line 23 a better condition. (Note that in line 22, the maximum heart rate was reached before the activity level reached the Hi point. In such a case one would expect a flat HR, and perhaps an end to the increase in activity before the Hi mark is reached). Note that a decreasing slope could represent either worsening chronotropic incompetence or improving cardiac function. If, for example, the patient is on an exercise regimen and is improving cardiac function this would appear as a decreasing slope.

Figure 3:
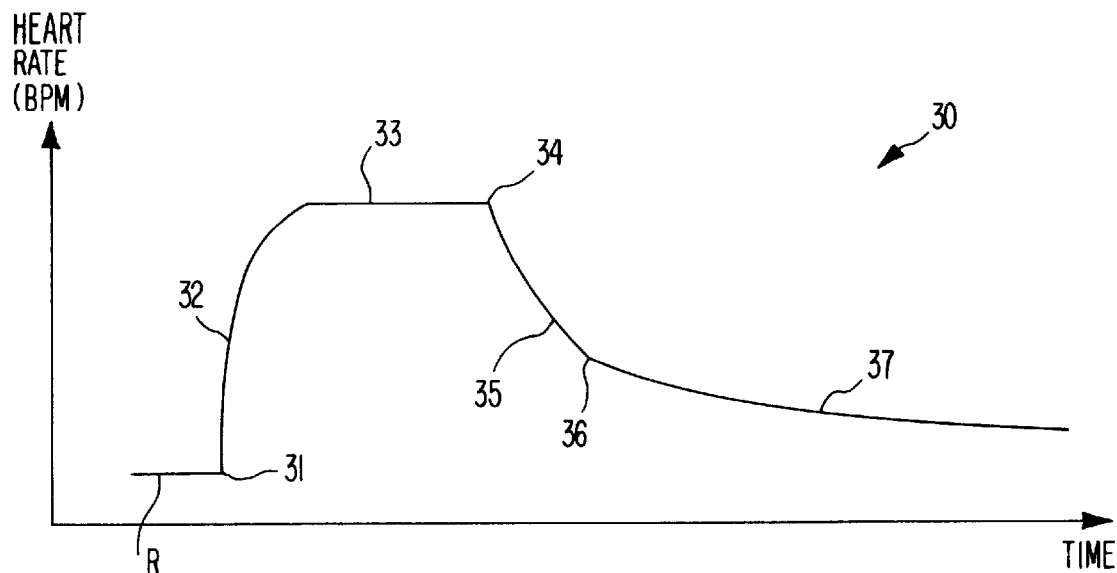
FIG. 3 is a graph of Heart Rate versus time.

Looking at a normal response curve of HR over time may clarify what we are looking for in the optimum HRAC variable. In FIG. 3, the resting heart rate is plotted on curve 30 at R, and at inflection point 31, the subject begins exercise, perhaps getting out of a chair to walk. The increase in heart rate will initially be steep with a relatively constant slope through most of segment 32, the walk will keep the heart rate constant at segment 33, and shortly after the walk, when the subject perhaps sits down again a return to resting rate will begin at point 34. Initially there may be a fairly steep recovery slope 35 toward the resting rate, then a more gradual recovery asymptotic segment 37. This figure is included to show that there are several points and segments along the activity response curve which could be adopted for the HRAC measure of HR. Thus, for example, the time from when the activity stops during segment 33 before the point 34 begins to show on the activity curve is known to change with cardiovascular strength, as is the slope of segment 35. A faster recovery toward resting rate, and here a steeper slope shows greater cardiovascular endurance, for another example. Therefore, the average HR in the first minute after exertion for greater than 5 minutes can be an excellent measure for HRAC. As will be shown later, this HRAC value, wherever it is taken if it is done consistently, can be most advantageously plotted over a long time frame.

Figure 4:
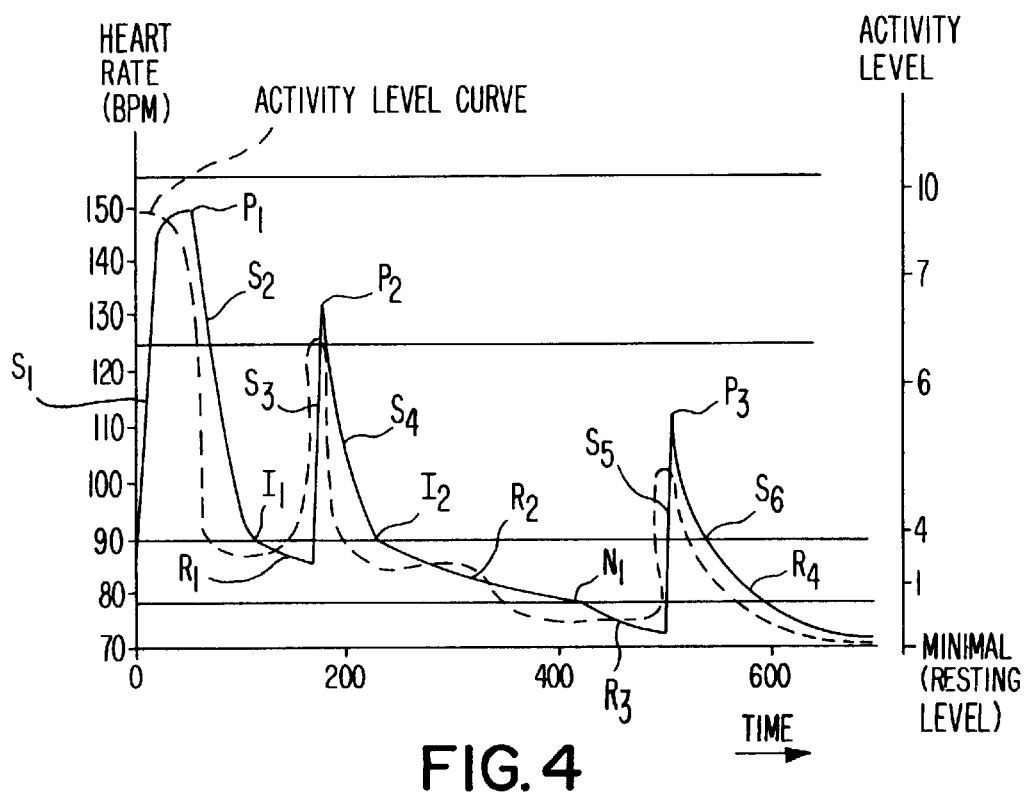
FIG. 4 is a graph of heart rate and activity versus time.

In FIG. 4, a series of activity cycles are shown in the dotted Activity Level curve, plotted from the left axis against time, in a compressed time frame. The HR response to the activity is plotted from the right axis. Review of this HR curve shows several segments over this 700 time unit time period that could be used for HRAC measurements. Thus at P1, where the patient may have reached maximum or at least a near plateau heart rate, the activity level is about 9. The speed of achieving the high heart rate is indicated in slope S1, and the similar slopes of S3, and S5 indicate fairly quick response to increasing activity levels. If a substantial change in this initial slope were seen over an extended period, a physician would have a good indication of a change in cardiac chronotropic competence for this patient. Similar considerations can be given to recovery periods S2, S4 and S6 as well as longer recovery slopes R1, R3 and R4.

To build a good HRAC chart, one method is to determine a single HRAC value for a period and take the same kind of determination in a series of subsequent periods. If for example the HRAC value is taken at specific times in each day and averaged for that day; then a series of days with such HRAC values taken at similar specific times and averaged produces a curve of HRAC average values over the series of days. If HRAC is measured any time activity gets over a certain level during a day and then all HRAC measurements are averaged on the median taken and similar measurements and averaging/median taking is done on subsequent days, a different but also useful series of HRAC values would be developed. The reader can easily imagine the nearly infinite variety of ways to compile a curve of HRAC values in a time series from this discussion in light of the rest of this disclosure. Again, the trend or slope or a derivative thereof or other calculated mathematical relationship will provide the measurement of interest.

Figure 5:
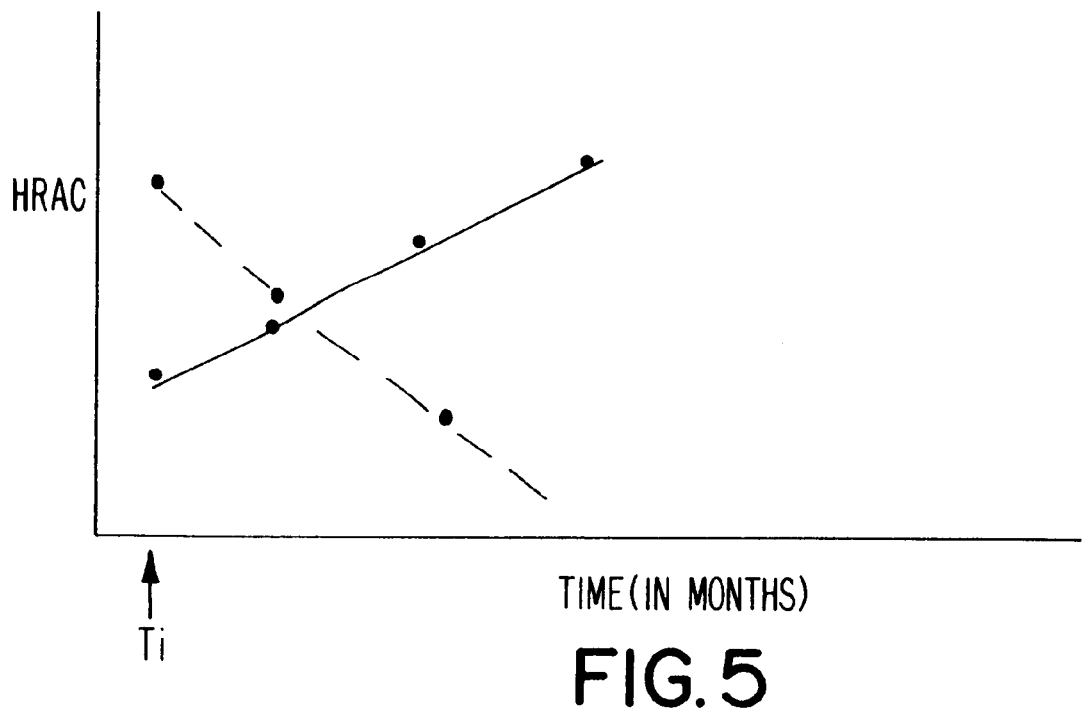
FIG. 5 is a graph of HRAC versus time.

Generally then, we are looking for a change in the HRAC measure over time, preferably measured in weeks or months. When patient condition is changing rapidly, we may be interested in shorter time frames, as in periods of days. In FIG. 5, the solid line shows a worsening CHF condition with the HRAC measure steadily increasing over time, indicating the patient is more and more dependent on heart rate to respond to the cardiac output needs of the patient. Along the dotted line, the patient has an HRAC measure that is falling consistently, potentially indicating that that patient has lost his ability to raise his heart rate responsive to cardiac demand. (Alternatively, it could be that cardiac function is improving, which can be confirmed with other tests). Because this measure has not heretofore been provided on a consistent basis, experience with this metric will be required to determine which segment of the activity and heart rate curves are best to use for determining the HRAC that gives the quickest indication of a change in CHF status. However, without this measure the alternative of occasional office visits leaves the potential for catching a patient at the point of losing chronotropic competence to mere chance.

It is also possible to incorporate into the implantable device containing the inventive ability to determine and store a measure of HRAC to use that measure reaching a preset level or maintaining a preset level over a preset period of time, programmable by a physician or set up during manufacture, to change the resolution of the storage of HRAC itself. Thus, if a patient is showing signs of deteriorating cardiac condition by the HRAC moving up by a given slope, the measurement and storage of HRAC may be increased. This could be done, for example, by increasing the sensitivity of HRAC recording trigger mechanisms (lower heart rate level to cause HRAC measurement, less of a period of time at a given activity level, et cetera), or by recording more HR levels at each trigger, or both. Furthermore, a patient trigger (using a magnet or a small transmitter to communicate with the implanted device) or a physician trigger to implement the desired granularity of HRAC recording times and levels may be used as well. It may also be noted that it is useful for a cardiac arrhythmia analysis to store activity level along with a cardiac electrogram when an arrhythmia is sensed since physicians consider arrhythmias during rest differently than those occurring during exercise in their diagnosis.

Again, in the general case, the progression of HRAC in a positive direction, indicating that heart rate is increasing at the given activity level selected shows a transition to or worsening of a cardiac condition. The decreasing HRAC curve (dotted line) shows a progressive chronotropic incompetence developing, or in other words the HR is failing to respond to the need for cardiac output believed to be occurring at times of patient activity at the chosen level. (A normal HRAC at a given activity or exercise level would be substantially flat over the same time period.)

Figure 7:
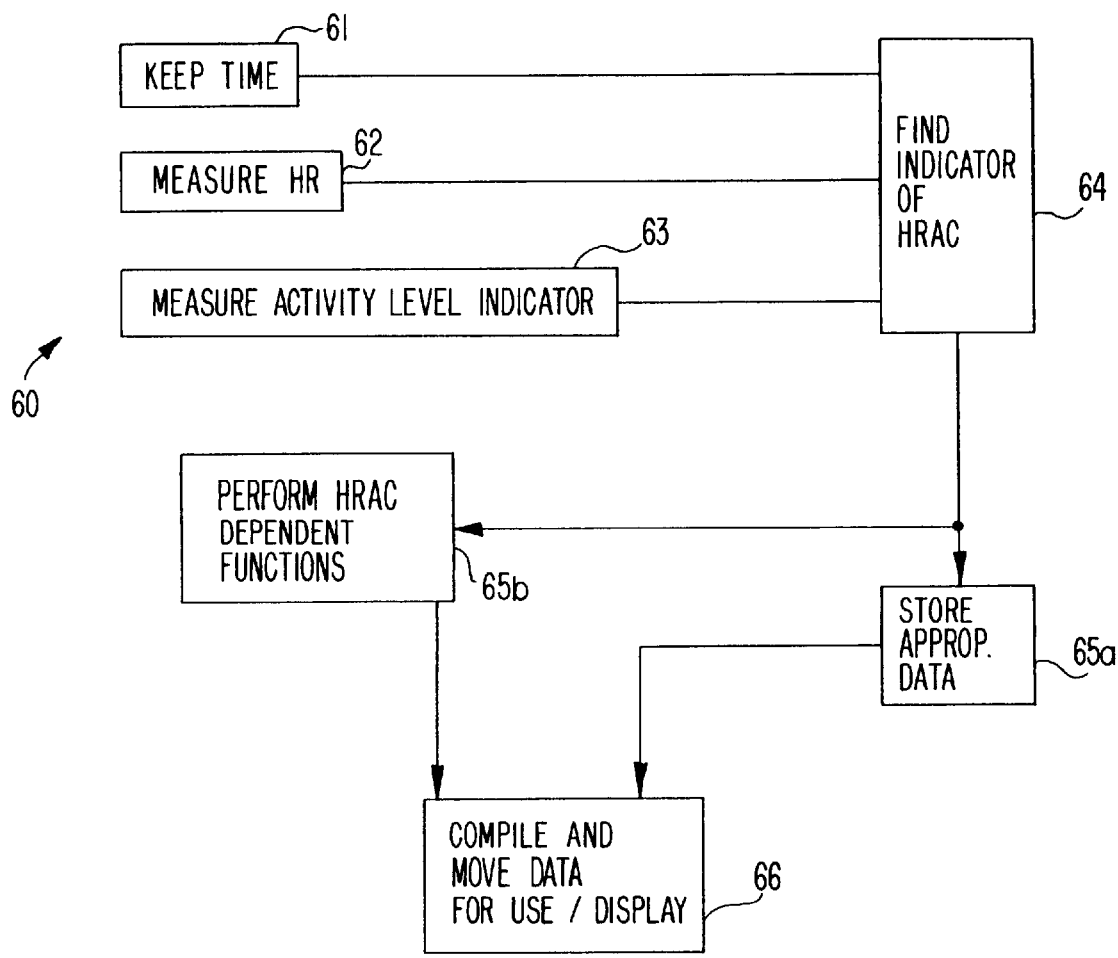
FIG. 7 is a flow chart.

In FIG. 7, the general process 60, is detailed. The implantable medical device which is constantly checking on the heart rate and activity level must also keep time. Thus steps 61–63 occur either intermedtly or continuously. To process the data, as mentioned earlier, a microprocessor or processing circuit will find an indicator of a good time to determine HRAC. This could be through determining a stable slope of increasing or decreasing HR over an appropriate length of time or by finding a given level of activity for an acceptably long duration. Then the processing circuit or microprocessor may choose to store whichever data is appropriate for the system designed. For example, if the system is designed to store HRAC values, the process would have to first compute the HRAC value for the time frame selected based on the trigger of sufficient activity or appropriate slope. Then it could store that data. If the system is designed to hold the raw data, it may mark the relevant raw data on the HR and activity level for storage in memory (Step 65a) until it is telemetered to an external processor that determines the HRAC values from the raw data. By advocating this much flexibility in the design implementation of step 64, the user of this concept can design devices to most efficiently employ this concept given the mission of the implanted device. If the device will be providing medications or other therapy including electrical stimulation to respond to increasing chronotropic incompetence, for example, we would want to design in the processing to determine the HRAC independent of any external device so that the implanted device could automatically adjust the dispensing of such medications or other therapy responsive to changes in HRAC without physician intervention. In such a device data on the HRAC should also be stored (Step 65a) for later analysis by the physician, even as it performs the HRAC dependent functions in step 65b. Such functions could include setting an alarm flag in memory or initiating a telemetry session to devices like TD in FIG. 6, to call the physician or medical system. In any event, the physician or medical system would most likely want to review the long term HRAC data through a process of compiling and removal to an external device such as device P the programmer in FIG. 6. for a useable display, and perhaps print out for the patient's file.

When an external device such as a programmer P (FIG. 6) requests a dump of the stored representations of value indicating the amount of patient activity, HR, and/or HRAC over time, it is formatted and sent over the communications channel by a communications circuit 83 to the external device so that it can be displayed in a human readable form. Alternatively, of course, the data can be sent via communications here simply represented by arrow C2 and arrow L1 to be stored in a telemetry device TD for later relaying to other devices by phone or other telemetry, here represented simply by arrow L2, for later or contemporaneous but distant display. The simplest preferred construction required for operative use of the invention is shown here. It is a simple matter to resend data over modern communications systems once it is retrieved in a machine readable format. As most implantable ICDs and pacemakers of today have microprocessors, memories and activity sensors and heart rate determining equipment, the addition of this invention to such devices would require no additional hardware, but mere software reconfiguration to accommodate the requirements of storing appropriate activity data in a useful manner so as a to be available for use in accord with this invention. It should also be noted that a clock circuit is also present in most implantable devices, and the timing of the output signals from the activity sensor and HR determination would be related to the passing of time. The microprocessor 77a or other processing circuits would employ either a system clock or a real time clock in a clock circuit CLK.

As mentioned, alternative forms of implant devices can be used. The Medtronic device REVEAL(TM), for example is fully implantable and similar to the device illustrated as device 71c, with a memory and processing circuitry for storing electrocardiograms, taken across two electrodes 79 and 72c. The addition of an additional circuit for sensing activity and appropriate circuitry to implement the storage of the relevant activity data in an appropriate manner would make this type of device another good candidate for the inventive features herein described. Also a drug pump such as device 71b when outfitted with the appropriate memory, processing and sensing circuits could do the same, as could other currently implantable devices. It should be noted that a device with nothing but an activity sensor, memory, HR monitor, a processor and some form of communications circuit would also be sufficient to perform the tasks required of this invention's implantable device. By using a kinetic power source, the dependence on a battery could be eliminated too and the device could be extremely small and unobtrusive, permitting the clinician to easily obtain patient consent to accept the implant.

Once the valuable functional status data is available, any communications system could be employed to get the information to the doctor, or to update the patient file. Any such uses of the information provided by this invention are contemplated.

It should be noted that activity levels and Heart Rate can be affected by a drug therapy intervention. As such, a device using the invention herein could provide a valuable research tool for eliminating the confounding data effects of heart rate, exercise, or the drug levels on the symptom under study. Also, the titration of drug therapy regimens can be enhanced with the data provided by this invention.

The HRAC data can also be coordinated with a display of other patient related data, including atrial fibrillation events, other tachy events of either chambers and the like. A device such as 71c which could track both arrhythmias and HRAC can be used to produce such a paired graph display.

A preferred activity signal is the one described in detail in co-pending U.S. application Ser. No. 09/078,221. This can produce a raw accelerometer/crystal signal which is first filtered using a bandpass filter and the total number of crossings above and below a fixed threshold is calculated for a time interval at every 2 seconds. The activity value is then calculated based on these 2 second activity counts.

While all these variations and more will naturally occur to one of ordinary skill in this art, we have found it to be perfectly acceptable to use a single axis accelerometer or piezocrystal with a value of 1.5 counts per minute as reasonable for cardiac patients. The amount of activity of a cardiac patient will generally be quite low on average and we want to pick up even small activities in the case of the CHF patient. Our studies indicated that an activity level of 95 steps per minute over the minutes walked of a healthy person was about 23, but at 60 steps per minute the average count was more like 5 or 8 counts per walked minute. Since the CHF patient will be doing few walks of more than a minute the expectation is that nearly all two second periods will register a zero activity signal, which was borne out through experiment. However, it should be recognized that if the small period chosen is larger, or the activity sensor more sensitive than what we used, a larger count may be expected, possibly necessitating an adjustment in the exclusion level above what we chose as 1.5 average counts per minute period. Similar adjustments to this value will occur to the reader without the need for undue experimentation. Therefore, in general, we are figuring on the basis of the number of short periods (like a 2 second interval), that a patient is determined to be active over the course of a first larger period, (more than 2 seconds). We may use this to trigger the timing of the collection of HR or we can use the change in HR to time the collection of activity level data.

Depending on the kind of display desired, we can telemeter or otherwise communicate the data from an implanted device monitoring activity data in the way we describe which includes any subset of the data or all of it. Preferably a display of the amount of activity in a day, averaged over a week will be displayed for a number of months in a display similar to the graphs illustrated in FIGS. 1–5. Additionally, this data can be printed out for storage and later use by reference to a patient's file.

Depending on the kind of display desired, we can telemeter or otherwise communicate the data from an implanted device monitoring HRAC or other data which includes any subset of the data or all of it. Preferably a display for a number of months in a display similar to the graph of FIG. 5 will be the result. Additionally this data can be printed out and stored for later use.

Many adaptations can be made upon the information provided by this invention. For one thing, a patient alarm may be sounded to incent the patient to comply with an exercise regimen or to call his doctor. Today small and low power piezo speakers with small speech producing circuitry are plentiful and inexpensive. If the data here shows a failure or inability of the patient to comply with an exercise regimen could actually speak to the patient and say things like, 'time to get on the treadmill' or 'time to go to the doctor' or something similar, based on the severity of the failure of the patient to achieve the activity goals set with his physician and programmed into the device. Additional patient signals like a buzzer, shaker, or even electric shock could be provided to get the patient's attention. As already mentioned, if a particular activity pattern is developing, and this device is included in a drug pump, or other therapy delivery device the drugs or other therapy the patient is receiving could be adjusted based on his activity level, the angle of its downward or upward slope, or other characteristics determinable based on this activity data set.

Also, if the device records arrhythmias sensed through auto triggering mechanisms or through patient activation of the event record we can report this data out with an indication of it's temporal correspondence to activity level. This can tell the physician whether the arrhythmia occurred during rest or activity. Arrhythmia monitoring background art, hereby incorporated by this reference includes U.S. Pat. Nos. 5,113,869; 5,313,953; and 5,086,772. Also incorporated by reference are the following patents on triggering recordings of arrhythmic events, both automatically and by patient activation; U.S. Pat. Nos. 4,086,916; 5,404,877 and 5,012,814.

Another less preferred embodiment would be to use an external device strapped or otherwise affixed to a patient's body to collect the activity data, (requiring of course some adjustment to the predetermined value for deciding whether a minute period qualified to be called active), but considering the difficulty in gaining patient compliance or comfort, we feel the implantable versions will be most efficacious.

This invention can be viewed from a broader perspective as well. Not only can the implanted device produce a HRAC measurement using various activity sensors and cardiac demand sensors for producing the so called "activity" signal values, but it may also take advantage of alternatives to HR for the "HR" signal values. These HR values can be thought of as a measure of the heart's ability to respond to demands for cardiac output. It is within this concept to employ alternatives to heart rate (HR) which is the easiest measure to employ. Thus, if the implanted device has a good measure of cardiac ability to respond, such as mixed venous oxygen saturation, coronary sinus oxygen saturation, or coronary sinus pH; a reliable valuation of the level of these measures could be substituted for HR at all points in the description above this paragraph and in the claims as well.

It has been noted that changes in oxygen saturation and pH could be measured in the coronary sinus in U.S. Pat. No. 5,199,428, issued to Obel and Bourgeois in 1993, incorporated herein by this reference. Oxygen sensors are described in Moore et al, and Baudino et al, U.S. Pat. Nos. 4,903,701 and 4,791,935, hereby incorporated by this reference in their entireties also. In Bensten et al. U.S. Pat. No. 5,882,936, and Saaski et al, U.S. Pat. No. 5,039,492, both also incorporated by reference, pH sensors are taught. Aldea U.S. Pat. No. 5,533,957, also incorporated by reference, shows the use of a catheter in the coronary sinus. Thus placing of an oxygen and/or pH sensor into the coronary sinus, to monitor the heart's own returned blood from in the coronary sinus for signs of cardiac deterioration can be done. (Likewise, an oxygen saturation sensor could be placed in the ventricle, or even a pressure sensor may be placed in the ventricle to provide similar or additional physiologic information to that received from the coronary sinus sensors just mentioned). When compared with the activity level, this indicator of cardiac ability to respond to cardiac demand during activity can provide alternative indicators to the actual heart rate for the HR part of the HRAC measurements. Alternatively, it can provide an implanted medical device with two HRAC measurements, one based on heart rate and another based on pH or oxygen saturation to provide additional clinical utility. Many variations on the teachings of this invention may fall within its ambit, but the invention is only limited by the following claims.

What is claimed is:

1. An implantable medical device for determining a Heart Rate Activity Coefficient (HRAC) comprising:
   a sealed housing adapted for chronic implantation into a living body, said housing having located therewithin,
      an activity sensor and activity level determining circuitry for producing an activity output signal having a value indicating a present level related to cardiac demand,
      a heart rate (HR) determining circuit for producing a HR output signal having a value indicating a present HR level,
      a timing circuit for use in relation of both said HR and activity output signal values to passing time which produces a timing signal,
      a processing circuit for relating said activity output signal and said HR output signals to a current time available by reference to said timing signal from said timing circuit, and
      a memory circuit for storing a time marked pair of values relating current HR output signals and activity output signals to a current time, in a series.

2. A system comprising the implantable medical device as set forth in claim 1 and further comprising an external processing unit having a processor circuit for reading said memory circuit and wherein said processing circuit comprises;
   an analysis means for analyzing either said HR output signal values over time or said activity signal values over time and determining therefrom, based on a predetermined formula, which of said time related pairs of said HR signal values and said activity signal values provides appropriate basis for producing an HRAC signal value from their combination, and then selecting said determined pairs of HR and activity signal values for combining, and
   a combination circuit means for combining said selected pairs of activity and HR signal value pairs to produce an HRAC signal value.

3. A system comprising the implantable medical device as set forth in claim 2 and further comprising an external processing unit having a processor circuit for reading said memory circuit and wherein said processing circuit comprises;
   an analysis means for combining said HRAC signal values in said series for display as a long term trend, and
   a display member for displaying long term trend.

4. A system as set forth in claim 2 wherein said external processor further comprises a display member for displaying HRAC values over time.

5. An implantable medical device as set forth in claim 1 wherein said heart rate (HR) determining circuit comprises:
   electrode means for receiving an electrocardiogram signal from a patient, and
   electrocardiogram signal analysis circuitry for determining heart rate from said electrocardiogram signal and for producing an output signal representing heart rate (HR).

6. The implantable medical device of claim 1 wherein said HR determining circuit further comprises means for measuring an alternative cardiac responsiveness signal comprising a combination of said HR signal and said which produces an augmented HR level signal and circuit means for producing said HR signal alternative cardiac responsiveness signal.

7. The implantable medical device of claim 1 wherein said HR determining circuit further comprises means for measuring an alternative cardiac responsiveness signal and employing said alternative cardiac responsiveness signal as said HR output signal.

8. The implantable medical device of claim 1 wherein the activity output signal is bolstered with a measure of cardiac demand.

9. The implantable medical device of claim 1 wherein measures of cardiac demand substitute for said activity output signal.

10. An implantable medical device as set forth in claim 1 wherein said processing circuit comprises;
    an analysis means for analyzing either said HR output signal values over time or said activity signal values over time and determining therefrom, based on a predetermined formula, which of said time related pairs of said HR signal values and said activity signal values provides appropriate basis for producing an HRAC signal value from their combination, and then selecting said determined pairs of HR and activity signal values for combining, and
    a combination circuit means for combining said selected pairs of activity and HR signal value pairs to produce an HRAC signal value.

11. An implantable medical device for determining a Heart Rate Activity Coefficient (HRAC) comprising:
    a sealed housing adapted for chronic implantation into a living body, said housing having located therewithin,
       an activity sensor and activity level determining circuitry for producing an activity output signal having a value indicating a present level related to cardiac demand,
       a heart rate (HR) determining circuit for producing a HR output signal having a value indicating a present HR level,
       a timing circuit for use in relation of both said HR and activity output signal values to passing time which produces a timing signal,
       a processing circuit for producing a HRAC signal by combining said HR output signal and said activity signal, and for relating said HRAC signal to a time determined by reference to said timing circuit output to produce a time coded HRAC signal output, iteratively, and a memory circuit for storing said iteratively produced time coded HRAC signal in a series.

12. The implantable medical device of any of claims 1–4 or 11 wherein said implantable medical device further comprises a device of the following set of devices:

a pacemaker, an ICD, a drug pump, a neurostimulator, an implantable electrocardiogram monitor, and an implantable physiologic sensor monitor.

13. The implantable medical device of any of claims 1–4 or 11 wherein said implantable medical device compasses a therapy delivery control circuit responsive to adjust therapy delivery based on said HRAC signal.

14. The implantable medical device of any of claims 1–4 or 11 wherein said implantable medical device further comprises Alarm circuit means for monitoring said HRAC signal level to determine if said HRAC signal level matches an alarm level, and for generating an alarm signal if said HRAC signal level does match said alarm level.

15. The implantable medical device of any of claims 1–4 or 11 wherein said implantable medical device further comprises Alarm circuit means for monitoring said HRAC signal level to determine if said HRAC signal level matches an alarm pattern, and for generating an alarm signal if said HRAC signal pattern does match said alarm pattern.

16. The implantable medical device of any of claims 1–4 or 11 wherein said implantable medical device further comprises telemetry circuit for communication of HRAC signal levels from said memory to an external device.

17. The implantable medical device of any of claims 1–4 or 11 wherein said implantable medical device further comprises telemetry circuit for communication of HRAC signal levels from said memory to an external device, and wherein said external medical device has communications means for communicating said HRAC signal levels across a Medical network wherein said medical network includes a display for displaying said HRAC signal levels for review by a physician.

18. A method of obtaining an HRAC measurement from an implantable medical device comprising:

determining that an HRAC measurement is needed by monitoring a physiologic signal for a predetermined indicator in said physiologic signal, when it is determined that an HRAC measurement is needed, simultaneously maintaining a time record and measuring a HR signal level and an activity signal level and relating said measurements to said time record, combining said HR signal level and activity signals for a related time period as indicated by said time record and from said combination producing a signal representing an HRAC measurement, and storing said HRAC signal measurement.

19. The method of claim 18 further comprising:

determining if said HRAC signal measurement that was stored matches a predetermined trigger pattern and if so, triggering the delivery of HRAC related therapy.

20. The method of claim 18 further comprising: evaluating said HRAC signal measurement and modifying a therapy delivery based on said evaluation.

21. The method of claim 18 further comprising:

determining if said HRAC signal measurement that was stored matches a predetermined trigger pattern and if so, triggering an alarm signal and, transmitting said alarm externally to said implantable medical device.

22. The method of claim 18 further comprising: producing a memory record of a set of HRAC measurements over a long time period.

23. The method of any of claims 18–22 further comprising the step of transferring said HRAC measurements from said implantable medical device to an external medical device, and compiling said HRAC measurements over a predetermined period of time, and displaying said HRAC measurements with respect to said predetermined period of time.

24. A method of obtaining an HRAC measurement from an implantable medical device comprising:

Setting a program for determining when to take HRAC measurements when it is determined that an HRAC measurement is needed, simultaneously maintaining a time record a HR signal level and an activity signal level and relating said measurements to said time record, Combining said HR signal level and activity signals for related time period as indicated by said time record and from said combination producing a signal representing an HRAC measurement, and storing said HRAC signal measurement.

25. The method of claim 24 wherein said setting step is automatic and based on the results of a step of making physiologic measurements.

26. The method of claim 25 wherein said physiologic measurements include HRAC.

27. The method of claim 24 wherein said settingstep is accomplished by programming intervention by a medical worker.

28. A method of obtaining an HRAC measurement from an implantable medical device comprising:

determining that an HRAC measurement is needed by monitoring a patient activation device for a signal indicating that the patient wants an HRAC measurement, and when it is determined that an HRAC measurement is needed, simultaneously maintaining a time record and measuring a HR signal level and an activity signal level and relating said measurements to said time record, combining said HR signal level and activity signals for a related time period as indicated by said time record and from said combination producing a signal representing an HRAC measurement, and storing said HRAC signal measurement.

* * * * *